(12) United States Patent
Pathak et al.

(10) Patent No.: US 10,271,770 B2
(45) Date of Patent: Apr. 30, 2019

(54) MEASUREMENT AND COLLECTION OF HUMAN TREMORS THROUGH A HANDHELD TOOL

(71) Applicant: VERILY LIFE SCIENCES LLC, Mountain View, CA (US)

(72) Inventors: Anupam J. Pathak, Mountain View, CA (US); Sarel Kobus Jooste, Mountain View, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 404 days.

(21) Appl. No.: 14/627,893

(22) Filed: Feb. 20, 2015

(65) Prior Publication Data

US 2016/0242679 A1    Aug. 25, 2016

(51) Int. Cl.
*A61B 5/11*     (2006.01)
*A61B 5/00*     (2006.01)
(Continued)

(52) U.S. Cl.
CPC .......... *A61B 5/1101* (2013.01); *A61B 5/0004* (2013.01); *A61B 5/0022* (2013.01); *A61B 5/1114* (2013.01); *A61B 5/1121* (2013.01); *A61B 5/1126* (2013.01); *A61B 5/4082* (2013.01); *A61B 5/4836* (2013.01); *A61B 5/6887* (2013.01); *A61B 5/7264* (2013.01); *A61B 17/00* (2013.01); *A61B 34/70* (2016.02); *A61B 34/75* (2016.02); *A61F 4/00* (2013.01);
(Continued)

(58) Field of Classification Search
None
See application file for complete search history.

(56) References Cited

U.S. PATENT DOCUMENTS

| 3,711,638 A | 1/1973 | Davies |
| 4,479,797 A | 10/1984 | Kobayashi et al. |

(Continued)

FOREIGN PATENT DOCUMENTS

| AT | 411 011 B | 9/2003 |
| CN | 203646979 U | 6/2014 |

(Continued)

OTHER PUBLICATIONS

*Thales Visionix Inc.* vs. *The United States*—Decision, Mar. 8, 2017, US Court of Appeals for the Federal Circuit.*
(Continued)

*Primary Examiner* — Rene T Towa
*Assistant Examiner* — Benjamin S Melhus
(74) *Attorney, Agent, or Firm* — Christensen O'Connor Johnson Kindness PLLC

(57) ABSTRACT

A technique for measuring and collecting human tremor data includes measuring motions of a handheld tool manipulated by a user while performing a task with the handheld tool. The motions are measured using an inertial measurement unit ("IMU") disposed within a handle of the handheld tool. Motion data of the motions is recorded to a motion log stored within a memory unit of the handheld tool. The motion data contains information for determining a severity of tremors that occurred while the user performed the task with the handheld tool. The motion log is communicated to a remote server for analysis.

12 Claims, 5 Drawing Sheets

(51) Int. Cl.
  *A61B 17/00* (2006.01)
  *A61F 4/00* (2006.01)
  *F16F 7/10* (2006.01)
  *A61B 34/00* (2016.01)
  *G16H 40/67* (2018.01)
  *A47G 21/02* (2006.01)

(52) U.S. Cl.
  CPC ........... *F16F 7/1005* (2013.01); *G16H 40/67* (2018.01); *A47G 21/02* (2013.01); *A47G 2200/046* (2013.01); *A61B 2017/00464* (2013.01); *A61B 2560/0431* (2013.01); *A61B 2562/0219* (2013.01)

(56) References Cited

U.S. PATENT DOCUMENTS

| | | |
|---|---|---|
| 4,766,708 A | 8/1988 | Sing |
| 5,148,715 A | 9/1992 | Blaser et al. |
| 5,316,479 A | 5/1994 | Wong et al. |
| 5,562,707 A | 10/1996 | Prochazka et al. |
| 5,691,898 A | 11/1997 | Rosenberg et al. |
| 5,934,250 A | 8/1999 | Fujikawa et al. |
| 6,234,045 B1 | 5/2001 | Kaiser |
| 6,238,384 B1 | 5/2001 | Peer |
| 6,458,089 B1 | 10/2002 | Ziv-Av |
| 6,547,782 B1 | 4/2003 | Taylor |
| 6,695,794 B2 | 2/2004 | Kaiser et al. |
| 6,697,048 B2 | 2/2004 | Rosenberg et al. |
| 6,697,748 B1 | 2/2004 | Rosenberg et al. |
| 6,704,001 B1 | 3/2004 | Schena et al. |
| 6,704,002 B1 | 3/2004 | Martin et al. |
| 6,730,049 B2 | 5/2004 | Kalvert |
| 6,740,123 B2 | 5/2004 | Davalli et al. |
| 6,743,187 B2 | 6/2004 | Solomon et al. |
| 6,946,812 B1 | 9/2005 | Martin et al. |
| 7,106,313 B2 | 9/2006 | Schena et al. |
| 7,224,642 B1 | 5/2007 | Tran et al. |
| 7,725,175 B2 | 5/2010 | Koeneman et al. |
| 7,883,479 B1 | 2/2011 | Stanley et al. |
| 8,286,723 B2 | 10/2012 | Puzio et al. |
| 8,308,664 B2 | 11/2012 | Pathak et al. |
| 9,074,847 B1 | 7/2015 | Sullivan et al. |
| 9,826,921 B2 | 11/2017 | Griffiths et al. |
| 2001/0012932 A1 | 8/2001 | Peer |
| 2003/0006357 A1 | 1/2003 | Kaiser et al. |
| 2003/0036805 A1 | 2/2003 | Senior |
| 2003/0209678 A1 | 11/2003 | Pease |
| 2005/0113652 A1 | 5/2005 | Stark et al. |
| 2006/0044942 A1 | 3/2006 | Brinn et al. |
| 2006/0241510 A1 | 10/2006 | Halperin et al. |
| 2007/0027367 A1* | 2/2007 | Oliver ................. A61B 5/0002 600/300 |
| 2007/0050139 A1 | 3/2007 | Sidman |
| 2007/0109783 A1 | 5/2007 | Wilson et al. |
| 2007/0270784 A1 | 11/2007 | Smith et al. |
| 2009/0031839 A1 | 2/2009 | Shimizu et al. |
| 2009/0173351 A1 | 7/2009 | Sahin et al. |
| 2009/0203972 A1 | 8/2009 | Heneghan et al. |
| 2009/0227925 A1 | 9/2009 | McBean et al. |
| 2009/0254003 A1 | 10/2009 | Buckman |
| 2009/0276058 A1 | 11/2009 | Ueda et al. |
| 2010/0013860 A1 | 1/2010 | Mandella et al. |
| 2010/0036384 A1 | 2/2010 | Gorek et al. |
| 2010/0079101 A1* | 4/2010 | Sidman ................. F16M 11/041 318/649 |
| 2010/0130873 A1 | 5/2010 | Yuen et al. |
| 2010/0145236 A1* | 6/2010 | Greenberg ........... A61B 5/1101 600/595 |
| 2010/0198362 A1 | 8/2010 | Puchhammer |
| 2010/0228362 A1 | 9/2010 | Pathak et al. |
| 2010/0274365 A1 | 10/2010 | Evans et al. |
| 2011/0112442 A1 | 5/2011 | Meger et al. |
| 2012/0139456 A1 | 6/2012 | Takano et al. |
| 2012/0249310 A1 | 10/2012 | Hotaling |
| 2013/0060124 A1 | 3/2013 | Zietsma |
| 2013/0060278 A1 | 3/2013 | Bozung et al. |
| 2013/0118320 A1 | 5/2013 | Richardson |
| 2013/0123666 A1 | 5/2013 | Giuffrida et al. |
| 2013/0123684 A1 | 5/2013 | Giuffrida et al. |
| 2013/0123759 A1 | 5/2013 | Kang |
| 2013/0281888 A1* | 10/2013 | Bender ................. A61B 5/1116 600/595 |
| 2013/0297022 A1 | 11/2013 | Pathak |
| 2014/0052275 A1 | 2/2014 | Pathak |
| 2014/0171834 A1 | 6/2014 | DeGoede et al. |
| 2014/0257047 A1 | 9/2014 | Sillay et al. |
| 2014/0257141 A1 | 9/2014 | Giuffrida et al. |
| 2014/0275817 A1* | 9/2014 | Script ...................... A61B 5/01 600/301 |
| 2014/0303605 A1 | 10/2014 | Boyden et al. |
| 2014/0303660 A1 | 10/2014 | Boyden et al. |
| 2015/0347204 A1* | 12/2015 | Stanley-Marbell ..... G06F 9/542 719/318 |

FOREIGN PATENT DOCUMENTS

| | | |
|---|---|---|
| JP | 2008-67936 | 3/2008 |
| JP | 2008-238338 | 10/2008 |
| JP | 2010-118798 A | 5/2010 |
| JP | 2011524192 A | 9/2011 |
| JP | 20144533127 A | 12/2014 |
| KR | 101659554 B1 | 9/2016 |
| WO | WO 00/052355 | 9/2000 |
| WO | WO 00/78263 A2 | 12/2000 |
| WO | WO 2013/049020 A1 | 4/2013 |
| WO | WO 2014/113813 A1 | 7/2014 |
| WO | WO 2015/003133 A1 | 1/2015 |

OTHER PUBLICATIONS

EP 16202985.4—Extended European Search Report, dated Mar. 23, 2017, 7 pages.

U.S. Appl. No. 13/935,387—Non-Final Office Action, dated Apr. 6, 2017, 14 pages.

Great Lakes Neurotechnologies, Press Release "Great Lakes Neurotechnologies Awarded Patent for Sensor Based Continuous Parkinsons Assessment During Daily Activities", Dec. 3, 2013, 2 pages www.glneurotech.com.

Pedley, Mark, "Tilt Sensing Using a Three-Axis Accelerometer", Freescale Semiconductor, Inc. Application Note, Document No. AN3461, Rev. 6, Mar. 2013, 22 pages.

Wireless & Mobile Human Monitoring, Latency Tech Note—Wireless Physiological Monitoring, Motion Sensor Latencies for Software Development, 4 pages retrieved from internet Feb. 3, 2015, http://glneurotech.com/bioradio/latency-tech-note/.

Wireless & Mobile Human Monitoring, Wireless motion sensor for 3D data acquisition via Bluetooth technology, Wireless Motion Sensor, 3 pages retrieved from internet Feb. 3, 2015, http://glneurotech.com/bioradio/physiological-signal-monitoring/wireless-motion-sensor/.

Sharon Smaga, "Tremor", American Family Physician, vol. 68, No. 8, Oct. 15, 2003, p. 1545-1552.

Louis, E.D., et al., "How common is the most common adult movement disorder" estimates of the prevalence of essential tremor throughout the world, Movement Disorders, 1998, 2 pages.

Louis, E.D., et al., "Correlates of Functional Disability in Essential Tremor", Movement Disorders, vol. 16, No. 5, 2001, pp. 914-920.

Diamond, A., et al., "The effect of deep brain stimulation on quality of life in movement disorders", Journal of Neurology, Neurosurgery & Psychiatry, 2005, 76(9): p. 1188-1193.

Ahmad Anouti, et al., "Tremor Disorders Diagnosis and Management", Western Journal of Medicine, 1995, 162(6): p. 510-513.

National Parkinson Foundation, Treatment options, 2009, <http://www.parkinson.org/Parkinson-s-Disease/Treatment >1 page.

E. Rocon, et al., "Theoretical Control Discussion on Tremor Suppression via Biomechanical Loading", 2003, 5 pages.

Caroline GL Cao, et al., "Robotics in Healthcare: HF Issues in Surgery," 2007, Online paper, http://ase.tufls.edu/mechanical/EREL/Publications/D-4.pdf, 33 pages.

(56) References Cited

OTHER PUBLICATIONS

Rubia P Meshack, et al., "A randomized controlled trial of the effects of weights on amplitude and frequency of postural hand tremor in people with Parkinson's disease", Clinical Rehabilitation, 2002, 16(5): p. 481-492.
Mario Manto, et al., "Dynamically Responsive Intervention for Tremor Suppression", IEEE Engineering in Medicine and Biology Magazine, 2003, 22(3): p. 120-132.
Eduardo Rocon, et al., "Mechanical suppression of essential tremor", The Cerebellum, 2007, 6(1): p. 73-78.
E. Rocon, et al., "Rehabilitation Robotics: a Wearable Exo-Skeleton for Tremor Assessment and Suppression", Proceedings of the 2005 IEEE International Conference on Robotics and Automation, 2005, p. 2271-2276.
Mark Heath, et al., "Design Considerations in Active Orthoses for Tremor Suppression: Ergonomic Aspects and Integration of Enabling Technologies", Assistive Technology—Shaping the Future AAATE, 2003, p. 842-846.
Olivier W. Bertacchini, et al., "Fatigue life characterization of shape memory alloys undergoing thermomechanical cyclic loading", Smart Structures and Materials 2003, 2003. 5053: p. 612-624.
DC-Micromotors, Application Datasheet, 0615 4.5S. 2010; 1 page available from: http://www.micromo.com.
Rodger J. Elble, "Physiologic and essential tremor", Neurology, 1986, 36(2): p. 225-231.
Cameron N. Riviere, et al., "Toward Active Tremor Canceling in Handheld Microsurgical Instruments", IEEE Transactions on Robotics and Automation, vol. 19, No. 5, Oct. 2003, p. 793-800.
Mitchell F. Brin, et al., "Epidemiology and Genetics of Essential Tremor", Movement Disorders, 1998. 13(S3): p. 55-63.
Rodger J. Elble, et al., "Essential tremor frequency decreases with time", Neurology, 2000, 55(10): p. 1547-1551.
Pathak et al. "Dynamic characterization and single-frequency cancellation performance of SMASH (SMA actuated stabilizing handgrip)." In: Modeling, Signal Processing, and Control for Smart Structures, Proceedings of SPIE, vol. 6926, 2008, pp. 692602-1 through 692602-12 [online]. Retrieved on Nov. 26, 2012 (Nov. 26, 2012). Retrieved from the Internet at URL:<http://144.206.159.178/ft/CONF/16413457/16413459.pdf>, entire document.
Shaw et al. "A reduced-order thermomechanical model and analytical solution for uniaxial shape memory alloy wire actuators." In: Smart Materials and Structures, vol. 18, 2009, pp. 1-21 [online]. Retrieved on Nov. 26, 2012 (Nov. 26, 2012). Retrieved from the Internet at URL:<hltp://deepblue.lib.umich.edu/bitstream/2027.42/65088/2/sms9_6_065001.pdf>, entire document, especially Fig. 1b; p. 3, col. 1.
Pathak, A. et al. "A Noninvasive Handheld Assistive Device to Accommodate Essential Tremor: A Pilot Study," Brief Report, Movement Disorders, May 2014; 29(6):838-42. doi: 10.1002/mds.25796.
Pathak, A. et al., "Handheld Tool for Leveling Uncoordinated Motion" U.S. Appl. No. 14/668,516, filed Mar. 25, 2015, whole document.
PCT/US2015/025781—International Preliminary Report on Patentability, dated Nov. 3, 2016, 9 pages.
CN 201280047035X—Third Office Action with English translation, dated Feb. 26, 2016, 8 pages.
PCT/US2016/013704—International Search Report and Written Opinion, dated Apr. 6, 2016, 19 pages.
Kostikis, N. et al.—"Smartphone-based evalution of parkinsonian hand tremor: Quantitative measurements vs clinical assessment scores", 2014 36th Annual International Conference of the IEEE Engineering in Medicine and Biology Society, IEEE, Aug. 26, 2014, pp. 906-909.

AU 2012316278—Australian Notice of Acceptance, dated Jan. 15, 2015, 2 pages.
AU 2012316278—Australian Notice of Grant, dated May 14, 2015, 2 pages.
KR 10-2014-7011131—First Office Action, with English translation, dated Aug. 20, 2015, 7 pages.
CN 2012-80047035.X—Second Chinese Office Action, with English Translation, dated Sep. 14, 2015, 11 pages.
JP 2014-533640—Notice of Allowance, dated Dec. 2, 2014, 3 pages.
PCT/US2014/045409, PCT International Preliminary Report on Patentability, dated Jan. 14, 2016, 8 pages.
U.S. Appl. No. 13/250,000—Notice of Allowance, dated Oct. 1, 2015, 5 pages.
U.S. Appl. No. 13/250,000—Non-Final Office Action, dated Oct. 19, 2016, 9 pages.
U.S. Appl. No. 13/935,387—Notice of Allowance, dated Oct. 7, 2015, 5 pages.
U.S. Appl. No. 13/935,387—Final Office Action, dated Oct. 21, 2016, 10 pages.
EP 12834632.7—Examination Report, dated Oct. 18, 2016, 5 pages.
JP 2016-000701—First Office Action, with English Translation, 15 pages, dated Jan. 10, 2017.
U.S. Appl. No. 13/250,000—Non-Final Office Action, dated Apr. 6, 2016, 13 pages.
U.S. Appl. No. 13/935,387—Non-Final Office Action, dated Apr. 11, 2016, 13 pages.
PCT/US2014/045409—International Search Report and Written Opinion of the International Searching Authority, dated Nov. 3, 2014, 9 pages.
PCT/US2012/057048—International Search Report and Written Opinion of the International Searching Authority, dated Dec. 17, 2012.
AU 2012316278—Australian Examination Report, dated Jul. 24, 2014, 3 pages.
PCT/US2012/057048, PCT International Preliminary Report on Patentability, dated Apr. 1, 2014, 5 pages.
U.S. Appl. No. 13/250,000—Restriction Requirement, dated Dec. 19, 2012, 9 pages.
U.S. Appl. No. 13/250,000—Non-Final Office Action, dated Apr. 5, 2013, 11 pages.
U.S. Appl. No. 13/250,000—Final Office Action, dated Mar. 20, 2014, 11 pages.
JP 2014-533640—First Japanese Office Action, dated Mar. 31, 2015, 5 pages.
U.S. Appl. No. 13/250,000—Non-Final Office Action, dated Apr. 2, 2015, 19 pages.
U.S. Appl. No. 13/935,387—Non-Final Office Action, dated Apr. 3, 2015, 25 pages.
CN 2012-80047035.X—First Chinese Office Action, with English Translation, dated Apr. 28, 2015, 10 pages.
EP 12834632.7—European Search Report, dated Jun. 10, 2015, 5 pages.
PCT/US2015/025781—International Search Report and Written Opinion of the International Searching Authority, dated Jul. 1, 2015.
Louis, E.D., "Essential Tremor", Handbook of Clinical Neurology, vol. 100, 2011, pp. 433-448.
Deuschl, G. et al., "Treatment of Patients with Essential Tremor", Lancet Neural of 2011, 10: 148-161.
Umemura, A. et al., "Deep Brain Stimulation for Movement Disorders: Morbidity and Mortality in 109 Patients", J Neurosurg 98: 779-784, 2003.
Notice of Reasons for Rejection for Japanese Patent Application No. 2017-542857 dated Sep. 12, 2018, 7 pages.

\* cited by examiner

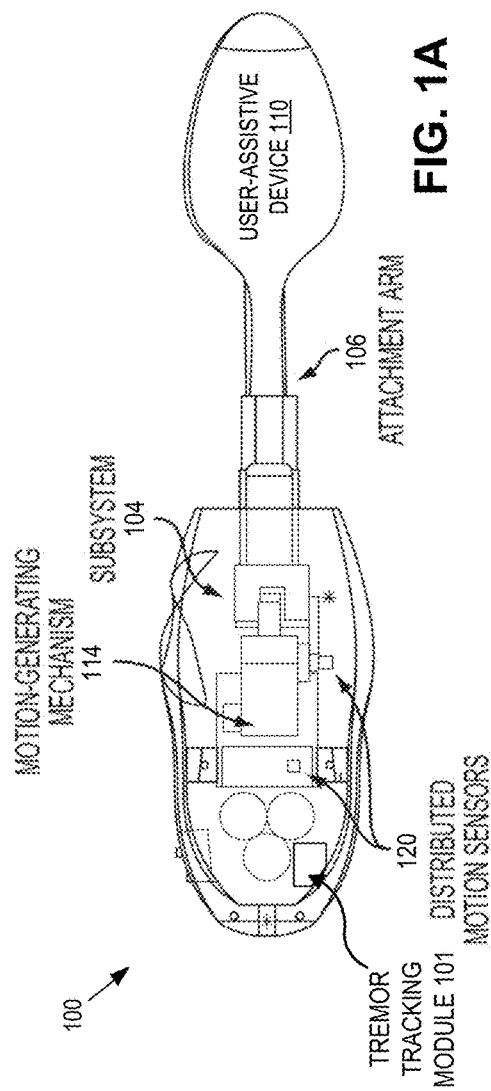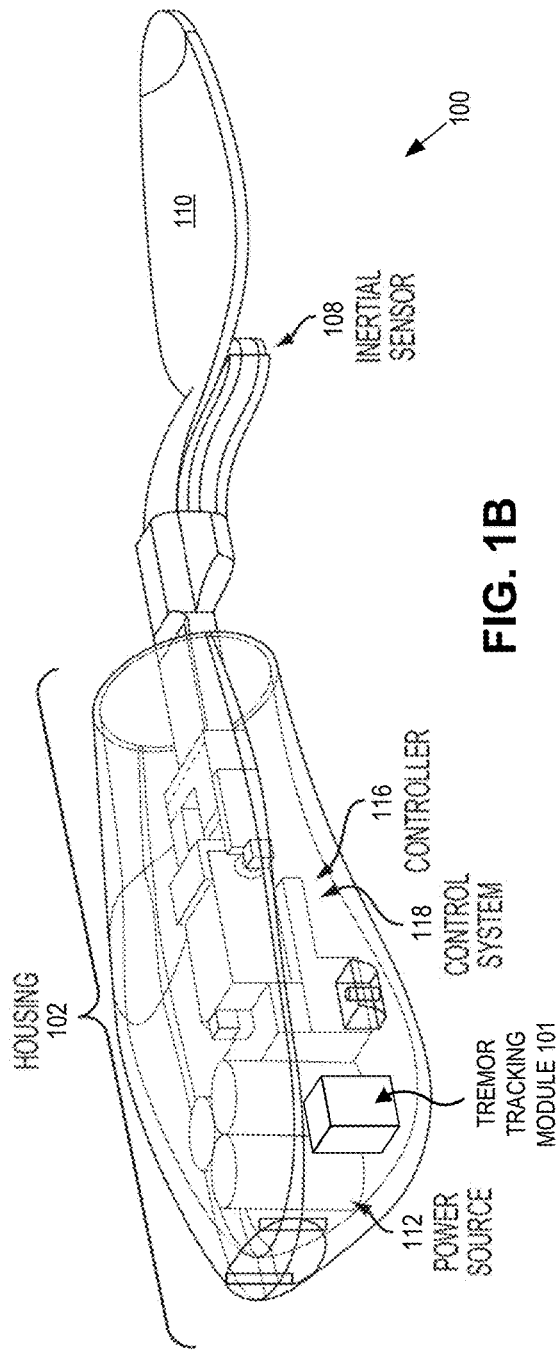
FIG. 1A
FIG. 1B

US 10,271,770 B2

MEASUREMENT AND COLLECTION OF HUMAN TREMORS THROUGH A HANDHELD TOOL

TECHNICAL FIELD

This disclosure relates generally to unintentional muscle movements, and in particular but not exclusively, relates to the measurement and tracking of unintentional muscle movements.

BACKGROUND INFORMATION

Movement disorders are often caused by chronic neurodegenerative diseases such as Parkinson's Disease ("PD") and Essential Tremor ("ET"). Both of these conditions are currently incurable and cause unintentional muscle movements or human tremors—uncontrollable rhythmic oscillatory movements of the human body. In many cases human tremors can be severe enough to cause a significant degradation in quality of life, interfering with daily activities/tasks such as eating, drinking, or writing.

Patients with movement disorders are typically diagnosed in a clinic using scales such as the Fahn-Tolosa-Marin Tremor Rating Scale for ET or the Unified Parkinson Disease (UPDRS) rating scale for PD. Both of these scales require a trained neurologist to complete and often rely on subjective assessments that occur over a brief period of time in the practitioner's office. Symptom severity at home is typically evaluated from the patient's self-reporting, which is also highly subjective and prone to error. This creates significant challenges when developing and evaluating long-term treatments or interventions for these diseases.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

FIG. 1A is a cross-sectional illustration of a handheld tool that measures and tracks unintentional muscle movements, in accordance with an embodiment of the disclosure.

FIG. 1B is a perspective view illustration of the handheld tool that measures and tracks unintentional muscle movements, in accordance with an embodiment of the disclosure.

DETAILED DESCRIPTION

Figure 2:
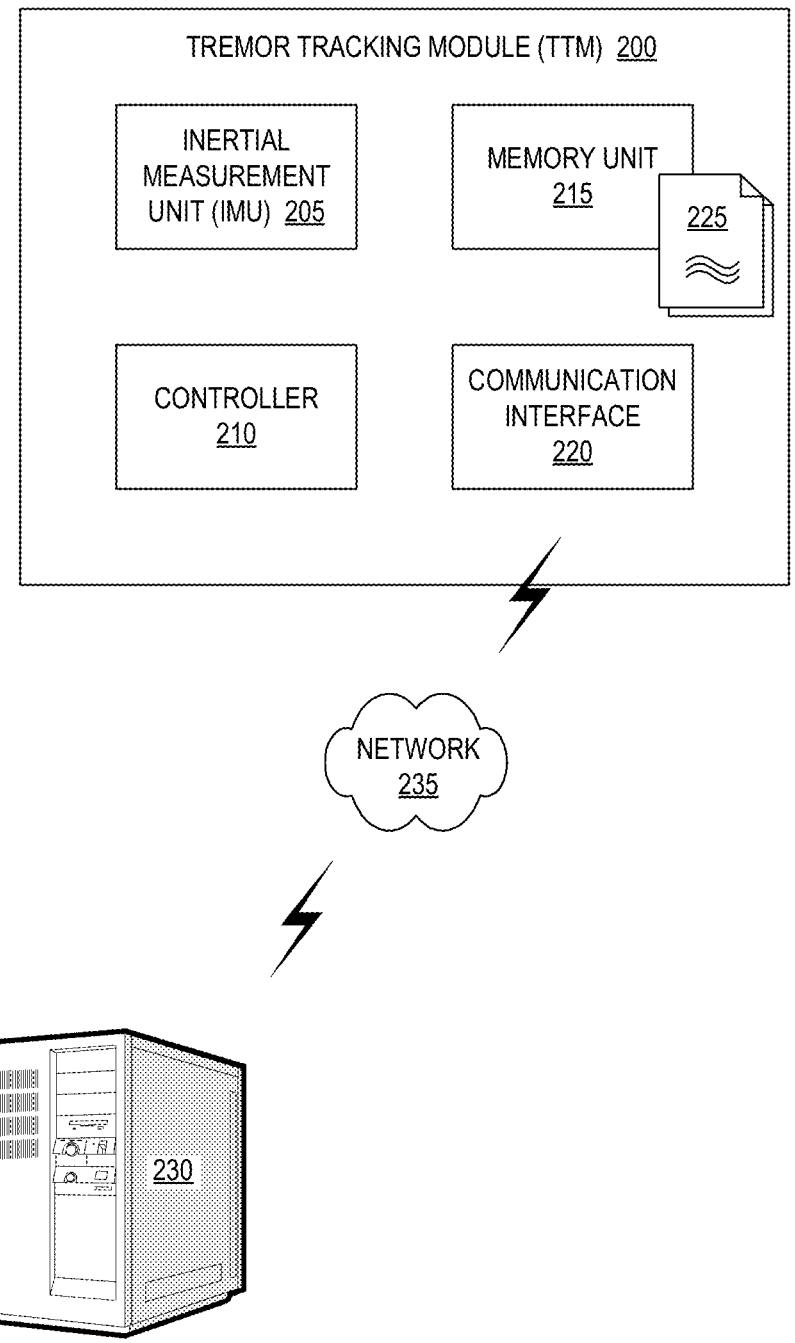
FIG. 2 is a functional block diagram illustrating a tremor tracking module, in accordance with an embodiment of the disclosure.

Embodiments of an apparatus, system and process for measuring, tracking, and analyzing unintentional muscle movements of a user while using a handheld tool to perform an ordinary activity are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

FIGS. 1A and 1B illustrate a handheld tool 100 that measures and tracks unintentional muscle movements, in accordance with an embodiment of the disclosure. FIG. 1A is a cross-sectional illustration of handheld tool 100 while FIG. 1B is a perspective view illustration of the same. Handheld tool 100 is also capable of detecting and compensating for unintentional muscle movement (tremors); however, it should be appreciated that various embodiments need not include the mechanisms and associated sensors for tremor compensation to implement the measurement, tracking, and/or diagnosing of tremors, even though both features are incorporated into the illustrated embodiment of handheld tool 100. Accordingly, the illustrated embodiment of handheld tool 100 includes a subsystem for measuring and tracking user tremors (e.g., a tremor tracking module) and a subsystem for detecting and compensating for those same tremors. These subsystems may have distinct components, or share some components such as power systems, memory, a controller, and may even share one or more sensors. In some embodiments, one or more components of the subsystem for detecting and compensating for tremors may be omitted.

Handheld tool 100 includes a housing 102, which functions as a handle for holding handheld tool 100. Handheld tool 100 also includes an attachment arm 106 coupled to the housing 102. Attachment arm 106 is configured to accept a user-assistive device 110 (e.g., a spoon in the illustrated embodiment) to its end distal from housing 102. Handheld tool 100 further includes a tremor tracking module ("TTM") 101 for measuring and tracking tremors. One or more components of TTM 101 are rigidly attached to housing 102 to measure and track tremors of the handle that the user holds. FIGS. 1A and 1B illustrate TTM 101 as a single block within housing 102; however, in other embodiments, TTM 101 includes several functional items that may assume a variety of different form factors and may further be spread throughout housing 102.

The illustrated embodiment of handheld tool 100 further includes a subsystem 104 for detecting and compensating for tremors of user-assistive device 110. In the illustrated embodiment, subsystem 104 includes at least one inertial sensor 108 placed along attachment arm 106 to measure absolute movement of attachment arm 106 and user-assistive device 110. Subsystem 104 further includes a portable power source 112, a motion-generating mechanism 114, a controller 116, a control system 118, and at least one distributed motion sensor 120 for measuring relative motion of attachment arm 106 relative to housing 102. As mentioned above, TTM 101 may share one or more of the components of subsystem 104 (e.g., power source 112, controller 116, etc.). In other embodiments, one or more of the components of subsystem 104 for compensating tremor motions may also be omitted (e.g., inertial sensor 108, motion-generating mechanism 114, etc.) while still implementing the tremor measurement and tracking functionality disclosed herein.

In one embodiment, attachment arm 106 is integrated with a specific type of user-assistive device 110 (spoon illustrated). In other embodiments, attachment arm 106 can receive a variety of different user-assistive devices 110 in a variety of ways including but not limited to a friction, snap, or other form of locking mechanism. Portable power source 112 may utilize a variety of options including but not limited to a rechargeable battery, a solar panel, etc.

The at least one inertial sensor 108 and the at least one distributed motion sensor 120 detect unintentional muscle movements and measure signals related to these unintentional muscle movements that are created when a user adversely affects motion of user-assistive device 110. These sensors also detect the motion of the stabilized output relative to the housing 102. Control system 118 sends voltage commands in response to the signals to the motion-generating mechanism 114 through the controller 116 to cancel the user's tremors or unintentional muscle movements. This cancellation maintains and stabilizes a position of the user-assistive device 110, keeping it centered relative to the housing 102.

One of ordinary skill in the art readily recognizes that a system and method in accordance with the present disclosure may utilize various implementations of controller 116, at least one inertial sensor 108, at least one distributed motion sensor 120, and control system 118 and that would be within the spirit and scope of the present disclosure. In one embodiment, controller 116 comprises an electrical system capable of producing an electrical response from sensor inputs such as a programmable microcontroller a field-programmable gate array (FPGA), an application specific integrated circuit ("ASIC"), or otherwise. In one embodiment, controller 116 comprises an 8-bit ATMEGA8A programmable microcontroller manufactured by Atmel due to its overall low-cost, low-power consumption and ability to be utilized in high-volume applications.

In one embodiment, the at least one inertial sensor 108 is a sensor including but not limited to an accelerometer, gyroscope, or combination of the two. In one embodiment, the at least one distributed motion sensor 120 is a contactless position sensor including but not limited to a hall-effect magnetic sensor. In one embodiment, the control system 118 is a closed-loop control system.

The closed-loop control system senses motion and acceleration at various points along handheld tool 100 and feeds detailed information into a control algorithm that moves motion-generating mechanism 114 appropriately to cancel the net effect of a user's unintentional muscle movements and thus stabilize the position of user-assistive device 110.

One of ordinary skill in the art will readily recognize that an apparatus, a system, or method as described herein may be utilized for a variety of applications. For example, various different user-assistive devices 110 may include a manufacturing tool, a surgical tool, a kitchen utensil (e.g., fork, knife, spoon), a sporting tool, a yard tool, a grooming tool (e.g., comb, nail clippers, tweezers, make-up applicator, etc.), or a dental hygiene tool (e.g., toothbrush, flossing tool, etc.). Thus, handheld tool 100 may be useful in not only improving the quality of life for the multitudes of individuals suffering from neurological motion disorders, but also in assisting in a variety of applications where physiological tremor is an issue including but not limited to manufacturing, surgical and public safety applications.

In one embodiment, handheld tool 100 stabilizes user-assistive device 110 about a neutral position (for example, $\theta=0$ may be selected or otherwise) using the at least one inertial sensor 108. To achieve this, the position of user-assistive device 110 is sensed along with the angle $\theta$. For this position sensing, the at least one inertial sensor 108 is placed along the attachment arm 106 and is used to measure the absolute motion of the user-assistive device 110 while providing low noise and sufficient sensitivity for the application. The direct sensor placement of the at least one inertial sensor 108 along attachment arm 106 gives a unique advantage to handheld tool 100 as it is extremely robust and does not rely on inverse kinematics/dynamics which may change depending on usage. Thus, as aforementioned, a variety of objects can be used to implement user-assistive device 110 without the need to pre-determine and pre-program the length and weight of user-assistive device 110 into the controller 116.

In the illustrated embodiment, the at least one distributed motion sensor 120 is located within the housing 102 which is located at the base of the handheld tool 100. The at least one distributed motion sensor 120 measures the relative motion of attachment arm 106 relative to the housing 102, wherein user-assistive device 110 is kept at a center position relative to housing 102. In one embodiment, the at least one distributed motion sensor 120 is at least one contactless hall-effect position sensor that provides angular feedback for control system 118 and relies on a changing magnetic field that is dependent on the actuation angle.

The changing magnetic field is detected by a strategically placed integrated circuit (IC) located within the at least one distributed motion sensor 120, whose analog output is read by controller 116, providing a completely non-contact angular detection that is capable of withstanding a large number of cycles. The at least one distributed motion sensor 120, with its contactless sensing methods, provides improved reliability over conventional direct-contact sensing methods such as potentiometers that wear over time.

In one embodiment, handheld tool 100 uses a combination of coreless micro-motors and miniature gear-reduction systems coupled to the coreless micro-motors using a coupling mechanism to implement motion-generating mechanism 114. Significant force of up to 10 newtons (N) can also be produced with these coreless micro-motors at the required tremor frequency of 0-5 hertz (Hz) through the use of a low-cost miniature gear-reduction system, with a total weight of only 6.5 grams (g). Furthermore, the power drawn from this technology is low, estimated at 0.5 watts (W).

FIG. 2 is a functional block diagram illustrating a TTM 200, in accordance with an embodiment of the disclosure. TTM 200 is one possible implementation of TTM 101 illustrated in FIGS. 1A and 1B. The illustrated embodiment of TTM 200 includes an inertial measurement unit ("IMU") 205, a controller 210, a memory unit 215, and a communication interface 220.

IMU 205 is disposed in rigid contact with housing 102 to directly measure the tremor motions of the handle and by extension the tremor motions of the user's hand. TTM 200 facilitates the measurement of human tremors while a user is performing an everyday task, such as eating or grooming (e.g., applying makeup). This is an important distinction over conventional in-clinic evaluations that simply measure the tremor of a hand that a patient is attempting to hold steady. Measurement and tracking of tremors while the patient is performing an everyday task measures the condition under real-world scenarios that are most adversely impacted by human tremors. Accordingly, TTM 200 can be embedded within everyday items or tools that are used routinely by patients to accurately measure and track their condition. This can lead to improved evaluations.

Not only can handheld tool 100 measure and track human tremors during a routine task, but it can conveniently do so over a period of time to obtain a more reliable dataset for statistical analysis. Furthermore, handheld tool 100 can be used at home where the user is more relaxed and under less stress than a formal evaluation in a practitioner's office. Data collection within the home environment along with larger datasets than can be obtained in-clinic, can provide more reliable data for evaluation of a patient's symptoms. Improved evaluation and diagnosis of the patient's tremors facilitate improved treatments and interventions of the various diseases and the conditions that cause human tremors.

IMU 205 may be implemented using variety of devices that measure motions of the handle of handheld tool 100. For example, IMU 205 may include one or more accelerometers that measure linear accelerations. In one embodiment, IMU 205 includes accelerometers capable of measuring translational accelerations of the handle in three orthogonal dimensions (e.g., x, y, and z dimensions). In one embodiment, IMU 205 includes a gyroscope to measure rotational motions (e.g., angular velocity about an axis) of the handle of handheld tool 100. In various embodiments, the gyroscope may be capable of measuring the rotational motions about one, two, or three orthogonal rotational axes. In one embodiment, IMU 205 includes a magnetometer to measure motions of the handle relative to a magnetic field (e.g., Earth's magnetic field or other externally applied magnetic field). In various embodiments, IMU 205 may include various combinations of some or all of the above listed motion measuring devices. Furthermore, these motion sensors may be disposed together on a common substrate that is rigidly attached to housing 102, or disposed throughout housing 102.

Controller 210 is communicatively coupled to IMU 205 and memory unit 215 to read motion data output from IMU 205 and store the motion data into memory unit 215. The motion data is collected over a period of time. For example, the motion data may be collected while the user performs an individual task, over the course of a day, a week, or other period of time. The collected motion data stored in memory unit 215 forms a motion log 225. In one embodiment, motion log 225 may contain enough information about the user's motions (linear accelerations, rotational velocities, durations of these accelerations/velocities, orientation relative to a magnetic field, etc.), based upon the motion data output from IMU 205, to recreate those motions using motion log 225. In one embodiment, motion log 225 may also record date/time stamps of when the motion data was collected and even include identifiers indicating the type of user-assistive device 110 that was attached to the handheld 100 when the motion data was collected. The type identifier provides an indication of the activity (e.g., eating with a fork, knife, or spoon, etc.) being performed by the user when the motion data was collected. This activity information and time/date stamps may be useful for the practitioner when evaluating the patient's motion log 225 to determine if the patient's tremors correlate to particular activities or time of day. In yet other embodiments, motion log 225 may also record battery voltage as a function of date/time, which may be used to analyzing system performance and battery usage. Tracking battery voltage is a sort of proxy for the amount of effort exerted by motion-generating mechanism 114 to stabilize user-assistive device 110. As such, tracking battery voltage or battery consumption correlates to the degree of a user's tremors since battery consumption will rise with increased tremors.

Controller 210 may be implemented with a programmable microcontroller, an FPGA, an ASIC, or other devices capable of executing logical instructions. The logical instructions themselves may be hardware logic, software logic (e.g., stored within memory unit 215 or elsewhere), or a combination of both. Memory unit 215 may be implemented using volatile or non-volatile memory (e.g., flash memory).

Communication interface 220 is communicatively coupled to output the motion log 225 from memory unit 215 to remote server 230 via network 235 (e.g., the Internet). In one embodiment, communication interface 220 is a wireless communication interface (e.g., Bluetooth, WiFi, etc.). For example, communication interface 220 may establish a wireless link to a user's cellular phone which delivers motion log 225 to server 230 via an installed tremor tracking application. The application may enable the user to control privacy settings, add comments about their usage of handheld tool 100, setup automatic periodic reporting of motion log 225, initiate a one-time reporting of motion log 225, along with other user functions. In yet another embodiment, communication interface 220 may be a wired communication port (e.g., USB port). For example, when the user connects handheld tool 100 to a charging dock to charge power source 112, communication interface 220 may also establish a communication session with remote server 230 for delivery of motion log 225 thereto.

Figure 3:
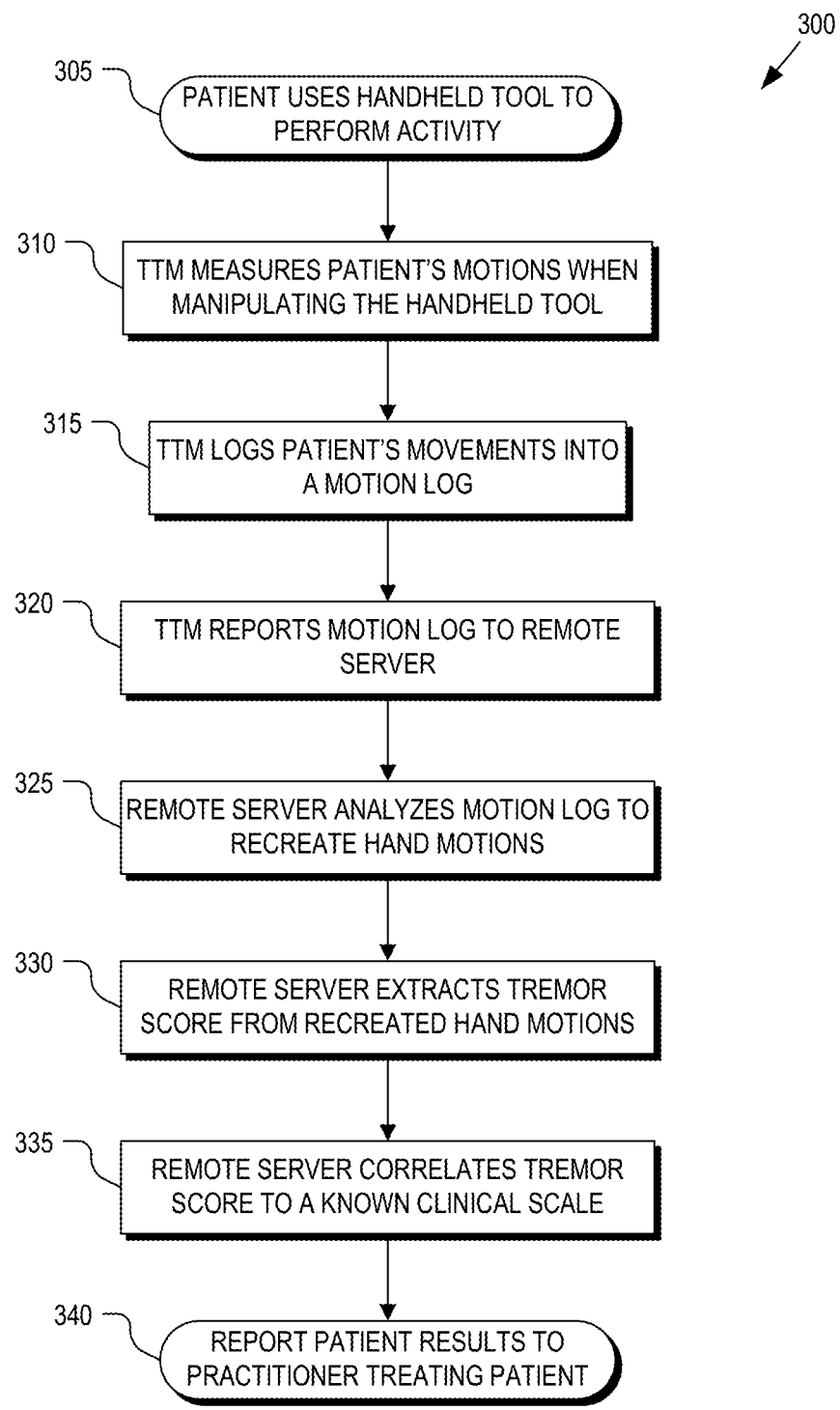
FIG. 3 is a flow chart illustrating a process for measuring, tracking, and analyzing unintentional muscle movements using a handheld tool, in accordance with an embodiment of the disclosure.

FIG. 3 is a flow chart illustrating a process 300 for measuring, tracking, and analyzing unintentional muscle movements (tremors) using handheld tool 100, in accordance with an embodiment of the disclosure. The order in which some or all of the process blocks appear in process 300 should not be deemed limiting. Rather, one of ordinary skill in the art having the benefit of the present disclosure will understand that some of the process blocks may be executed in a variety of orders not illustrated, or even in parallel.

In a process block 305, a patient (user) uses handheld tool 100 to perform a task or activity, such as a routine everyday activity including eating or grooming. Of course, handheld tool 100 may also be used for other non-routine activities, as described above. While performing this activity, TTM 101 measures the patient's motions as the patient manipulates handheld tool 100 (process block 310). TTM 101 directly measures the motions, including tremors, of the handle of handheld tool 100. In some embodiments, handheld tool 100 may also perform simultaneous active stabilization of user-assistive device 110 to reduce the impact of the patient's human tremors. In other embodiments, handheld tool 100 either does not include active stabilization or the active stabilization functionality may be disabled.

While the patient manipulates handheld tool 100, IMU 205 actively measures the tremors and outputs motion data indicative of the user's motions, including their tremors. In one embodiment, the sensors of IMU 205 are sampled at a rate of 50 times per second. Of course, other sampling rates may be implemented. In process block 315, the motion data is stored into memory unit 215 as motion log 225. In one embodiment, the generation of motion log 225 within memory unit 215 is orchestrated by controller 210. As mentioned above, motion log 225 may be populated with additional information such as time/date stamps, type of user-assistive device 110 attached to attachment arm 106, or otherwise. The type of user-assistive device 110 may be collected by incorporation of an electronic readable identifier (e.g., RFID tag, an electronic readable serial number, etc.) disposed in or on user-assistive device 110, by user input using a cellular phone application, or otherwise. In one embodiment, motion log 225 is further populated with data that is indicative of an amount of correction imparted by motion-generating mechanism 114 and/or sensor data from inertial sensor 108 and distributed motion sensors 120. This additional data contains information about how much stabilization handheld tool 100 imparted while the user performed a given task and can provide useful information for analyzing the user's tremors.

In a process block 320, TTM 101 reports motion log 225 to remote server 230 via communication interface 220 and network 235. The reporting of motion log 225 may be periodic, user initiated, initiated when memory unit 215 reaches a threshold capacity, initiated when handheld tool 100 is charged, or otherwise. In one embodiment, controller 210 facilitates the transmission of motion log 225 out communication interface 220 in cooperation with an external user application.

In a process block 325, remote server 230 analyzes motion log 225 to recreate the user motions, including the tremor motions, recorded while the user manipulated handheld tool 100 while performing a task. Transmission of motion log 225 to remote server 230 enables in-home data collection and external analysis and evaluation of the patient's condition.

The analysis of the motion data within motion log 225 may be performed using a variety of different algorithms to estimate the user's motion. For example, in a case where IMU 205 includes a tri-axial accelerometer and a tri-axial gyroscope the following analysis is one example analysis that can be performed by remote server 230.

Since an accelerometer and a gyroscope do not directly sense the user's hand position, equations of motion are used to estimate the amplitude and frequency of the user's hand tremor. The below equations account for errors introduced in the accelerometer signals—due to centripetal acceleration and gravitational artifacts introduced by tilt. Once these errors are removed, the acceleration data is transformed from the time domain into the frequency domain, using a Fast Fourier Transform ("FFT"). By extracting the peak of the resulting spectrum, the dominant tremor frequency can be calculated as well as an estimate of the amplitude of the hand's acceleration. Equations of motion for vibrating objects can be used to then calculate the amplitude of the hand's position.

Figure 4:
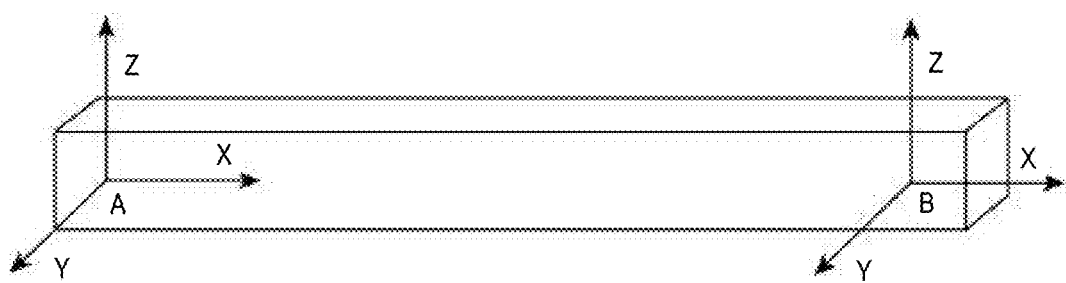
FIG. 4 illustrates an example rigid body assumption of a handheld tool, in accordance with an embodiment of the disclosure.

In one embodiment, we can start by modeling handheld tool 100 as a rigid body undergoing both translational and rotational motion. FIG. 4 illustrates an example rigid body assumption for handheld tool 100. Point A is where IMU 205 is positioned (sensing angular rate and acceleration), and point B is where motion is being estimated (tip of a spoon, for example). The acceleration at point B can be related to the acceleration at A with the following equations:

$$\dot{B}'_x = \dot{A}'_x - r\dot{\theta}_z^2 - r\dot{\theta}_y^2 + g\theta_y \quad \text{(Equation 1)}$$

$$\dot{B}'_y = \dot{A}'_y + r\dot{\theta}^o{}_2 + g\theta_x \quad \text{(Equation 2)}$$

$$\dot{B}'_z = \dot{A}'_z + r\dot{\theta}'_y \quad \text{(Equation 3)}$$

The terms leading to error include the terms for centripetal acceleration (Equation 1) as well as terms due to the gravitational vector shifting due to tilt (Equations 1 and 2). The latter error source relies on estimates of the device's pitch and roll (defined as $\theta_y$ and $\theta_x$).

The motion of point B by can be estimated as a single-frequency sinusoid (due to human tremor) with the following solution (using a trig identity):

$$B(t) = \overline{B}[\cos(\omega t) + i\sin(\omega t)] = \overline{B}e^{i\omega t} \quad \text{(Equation 4)}$$

The same can be written for angular rotation:

$$\theta(t) = \overline{\theta}[\cos(\omega t) + i\sin(\omega t)] = \overline{\theta}e^{i\omega t} \quad \text{(Equation 5)}$$

Using the exponential form and taking the time derivatives gives (for Equation 4):

$$B'(t) = \overline{B}i\omega e^{i\omega t} \quad \text{(Equation 6)}$$

and $$B'(\dot{t}) = \overline{B}(-\omega^2)e^{i\omega t} \quad \text{(Equation 7)}$$

where $\overline{B}$ is the amplitude of the sinusoid and $\omega$ is the angular frequency.

Two relationships can be obtained by inspecting Equation 4, 6, and 7. First, for a single sinusoid, the angular rate is proportional to displacement signal, scaled by the sinusoidal frequency and shifted 90 degrees out of phase. The second relationship is that the acceleration is the negative of the displacement signal, scaled by the square of the frequency.

A first order estimate of the user's motion can be done from the assumption that 1) the handheld tool 100 is a rigid body and 2) the tremor is sinusoidal in nature. From the first assumption, the motion of the tip of a rigidly connected spoon can be calculated from the following relationship:

$$B_i = A_i + L \sin \theta_j \quad \text{(Equation 8)}$$

i is the axis of interest (x, y, z), and j is the orthogonal axis of rotation inducing the motion. Equations 1, 2, and 3, can be used to estimate the motion of A (correcting for the terms introducing error). The amplitude of A and $\theta$ can be estimated by taking the FFT of the accelerometer and gyroscope signals, finding the peak, and then using the relationships of Equations 6 and 7 to calculate the magnitude of B.

The orientation of handheld tool 100 (relative to an inertial coordinate system) using the accelerometer and gyroscope signals can be performed. One way to accomplish pitch and roll estimation is to estimate a gravitational vector through a combination of a low pass filter of the accelerometer sensor and an integration of the gyroscope sensor. To calculate the pitch and roll of the device, rotation matrices are used to estimate the following equations:

For pitch:

$$\tan\theta_y = \frac{-g_x}{\sqrt{g_g^2 + g_z^2}} \quad \text{(Equation 9)}$$

and for roll:

$$\tan\theta_x = \frac{g_y}{g_z} \quad \text{(Equation 10)}$$

The vector g is calculated through a complementary filter (can also use a Kalman filter), using both the gyroscope and accelerometer signals as inputs. An alternate way to estimate the pitch and roll angles is to use a magnetometer as a third sensor input. It should be appreciated that the above analysis is only one example of analyzing motion log 225 to recreate the motions of handheld tool 100. Other techniques may be implemented.

Returning to process 300 illustrated in FIG. 3, remote server 230 extracts a tremor score from the recreated hand motions, in a process block 330. For example, the tremor score may be based upon the frequency and amplitude of the user's tremors as determined by the above analysis. In process block 335, the tremor score is correlated to a known clinical scale, such as the Fahn-Tolosa-Marin Tremor Rating Scale or the Unified Parkinson Disease (UPDRS) rating scale.

Finally, a report of the patients results, including their tremor score, is communicated to the practitioner treating the patient. In one embodiment, this report is communicated electronically over the Internet in a secure manner to the practitioner.

Figure 5:
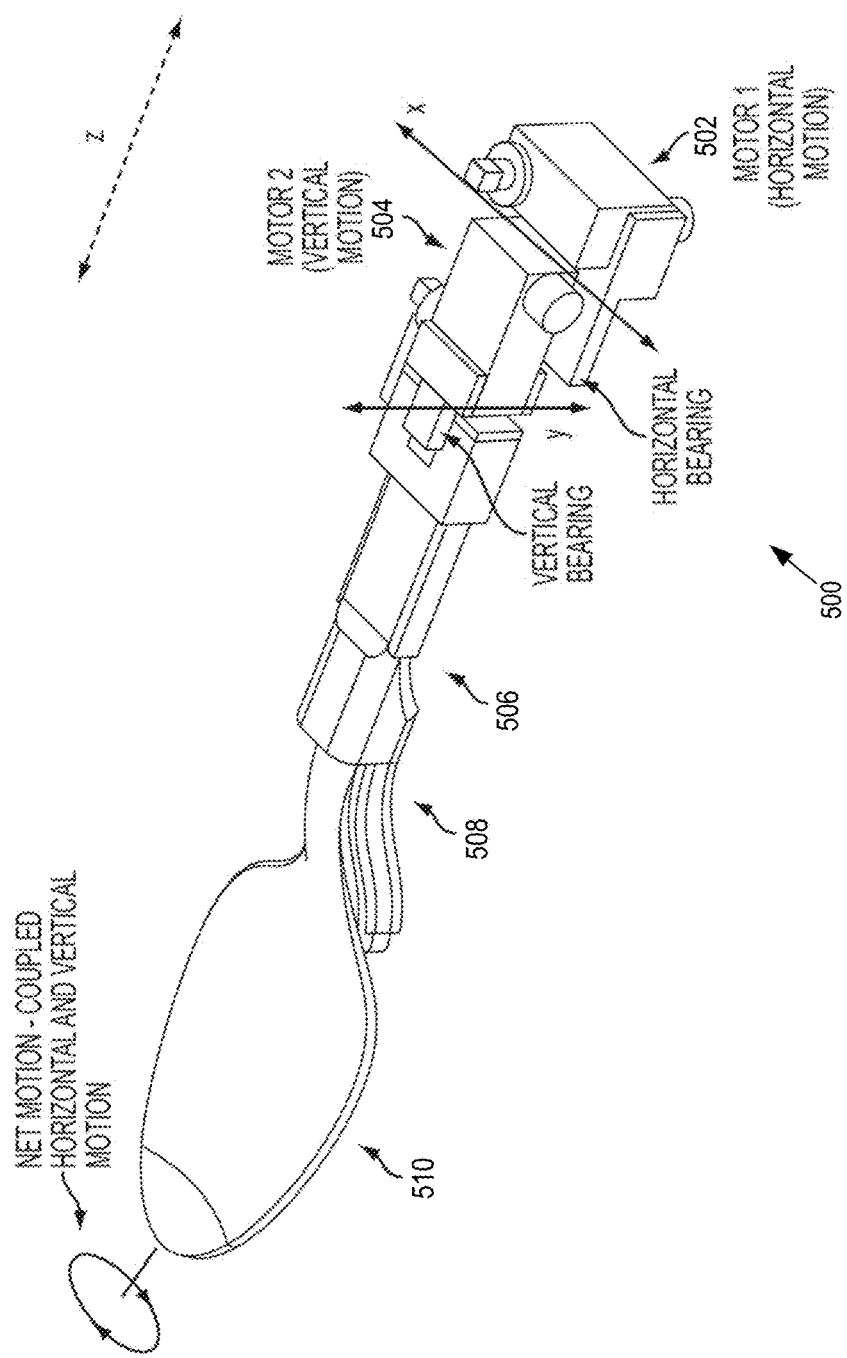
FIG. 5 is a perspective view illustration of a motion generating mechanism of a handheld tool that compensates for unintentional muscle movements, in accordance with an embodiment of the disclosure.

FIG. 5 is a perspective view illustration of a motion generating mechanism 500 of a handheld tool that compensates for unintentional muscle movements, in accordance with an embodiment of the disclosure. Motion generating mechanism 500 is one possible implementation of motion generating mechanism 114 illustrated in FIGS. 1A and 1B.

Motion-generating mechanism 500 includes a first miniature gear-reduction system coupled to a first coreless micro-motor 502 and a second miniature gear-reduction system coupled to a second coreless micro-motor 504. At least one inertial sensor 508 is placed along an attachment arm 506. The attachment arm 506 is configured to accept a user-assistive device 510 thereto.

The first coreless micro-motor is capable of producing rotary motion in the horizontal (x) direction. This rotary motion is imparted to the second coreless micro-motor through a rigid connection that is supported by a horizontal bearing. The second coreless micro-motor is capable of producing motion in the vertical (y) direction. This motion from the second coreless micro-motor is supported by a vertical bearing.

A coupling mechanism is used to combine the horizontal and vertical motions of the two separate coreless micro-motor/miniature gear-reduction systems 502 and 504. This combination results in a bi-directional circular motion of the user-assistive device 510 (in the illustrated embodiment, a spoon). One of ordinary skill in the art readily recognizes that a system and method in accordance with the present disclosure may utilize a variety of coupling mechanisms including but not limited to sliding bearing mechanisms, gimbal structures, or bellows structures and that would be within the spirit and scope of the present disclosure.

In the motion-generating mechanism 500, two degrees of freedom are generated from the two separate coreless micro-motor/miniature gear-reduction systems 502 and 504. Additional degrees of freedom (e.g., a third in the z-direction) can be added to the motion-generating mechanism 500 by adding motion to the output of the first coreless micro-motor or the output of the second coreless micro-motor.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method performed by a handheld tool that stabilizes unintentional muscle tremors, the method comprising:
   measuring the unintentional muscle tremors imparted to the handheld tool when manipulated by a user while the user performs a task with the handheld tool, wherein the unintentional muscle tremors are measured using a motion sensor attached to a handle of the handheld tool;
   stabilizing a user-assistive device extending from the handle with at least one motor disposed within the handheld tool and coupled to the user-assistive device, wherein the stabilizing is based at least in part upon the unintentional muscle tremors;
   recording motion data of the unintentional muscle tremors to a memory unit disposed on-board of the handheld tool, wherein the motion data is recorded into the memory unit by a controller disposed within the handle and coupled to the motion sensor and the memory unit, wherein the motion data includes an indication of an amount of correction imparted by the at least one motor while the user performs the task; and
   generating a motion log within the memory based upon recording the motion data of the unintentional muscle tremors, wherein generating the motion log includes generating a dataset for analysis of a severity of the unintentional muscle tremors; and
   communicating the motion log to a remote server.

2. The method of claim 1, wherein the motion sensor comprises an inertial measurement unit (IMU) that includes sensors to measure both translational and rotational motions of the handheld tool.

3. The method of claim 2, wherein the IMU includes one or more of an accelerometer, a gyroscope, or a magnetometer being mounted to the handle of the handheld tool to measure both the translational and the rotational motions of the handheld tool.

4. The method of claim 1, wherein the handheld tool comprises a kitchen utensil and the task comprises eating with the kitchen utensil.

5. The method of claim 1, wherein the handheld tool includes an attachment arm for removably attaching different user-assistive devices to a distal end of the attachment arm, the method further comprising:

determining, by the controller, a type of the user-assistive device coupled to the distal end of the attachment arm;

recording, by the controller, the type of the user-assistive device coupled to the distal end of the attachment arm while performing the task in the memory unit, wherein the type of the user-assistive device provides an indication of the task; and communicating the type of the user-assistive device with the motion log to the remote server.

6. The method of claim 5, wherein the type of the user-assistive device includes an indication of at least one of a fork, a knife, or a spoon.

7. The method of claim 1, wherein communicating the motion log to the remote server for analysis comprises:

establishing a wireless linking to a cellular phone; and uploading the motion log to the remote server over the wireless link in response to user commands received from the cellular phone via the wireless link.

8. The method of claim 1, wherein communicating the motion log to the remote server for analysis comprises:

communicating the motion log to the remote server upon the handheld tool being coupled to a charging dock that charges an internal battery of the handheld tool.

9. The method of claim 1, further comprising:

measuring a battery voltage of a battery disposed within the handle while the user performs the routine task;

recording, with the controller, the battery voltage with time stamps into the memory unit along with the motion log to track battery consumption as a function of time, wherein the battery consumption as the function of time correlates to the severity of the tremors and is indicative of an amount of correction imparted by the at least one motor while stabilizing the tremor motions.

10. A method performed by a handheld tool that stabilizes unintentional muscle tremors, the method comprising:

measuring the unintentional muscle tremors imparted to the handheld tool when manipulated by a user while the user performs a task with the handheld tool, wherein the unintentional muscle tremors are measured using a motion sensor attached to the handheld tool;

stabilizing a user-assistive device extending from a handle of the handheld tool with at least one motor disposed within the handle of the handheld tool and coupled to the user-assistive device to stabilize the unintentional muscle tremors imparted to the handle;

recording motion data of the unintentional muscle tremors to a memory unit disposed on-board of the handheld tool, wherein the motion data is recorded into the memory unit by a controller disposed within the handle and coupled to the motion sensor and the memory unit, wherein the motion data includes an indication of an amount of correction imparted by the at least one motor;

generating a motion log within the memory based upon the motion data, wherein the motion log provides a dataset for analysis of a severity of the unintentional muscle tremors while performing the task; and communicating the motion log to a remote server.

11. At least one machine-accessible storage medium that provides instructions that, when executed by a handheld tool, will cause the handheld tool to perform operations comprising:

measuring unintentional muscle tremors imparted to the handheld tool when manipulated by a user while the user performs a task with the handheld tool, wherein the unintentional muscle tremors are measured using a motion sensor attached to the handheld tool;

stabilizing a user-assistive device extending from a handle of the handheld tool with at least one motor disposed within the handle of the handheld tool and coupled to the user-assistive device to stabilize the unintentional muscle tremors imparted to the handle;

recording motion data of the unintentional muscle tremors to a memory unit disposed on-board of the handheld tool, wherein the motion data includes an indication of an amount of correction imparted by the at least one motor;

generating a motion log within the memory based upon the motion data, wherein the motion log provides a dataset for analysis of a severity of the unintentional muscle tremors while performing the task; and communicating the motion log to a remote server.

12. At least one machine-accessible storage medium that provides instructions that, when executed by a handheld tool, will cause the handheld tool to perform operations comprising:

measuring unintentional muscle tremors imparted to the handheld tool when manipulated by a user while the user performs a task with the handheld tool, wherein the unintentional muscle tremors are measured using a motion sensor attached to the handheld tool;

stabilizing a user-assistive device extending from a handle of the handheld tool with at least one motor disposed in the handle and coupled to the user-assistive device to stabilize the unintentional muscle tremors imparted to the handle;

measuring a battery voltage of a battery of the handheld tool while the user performs the task; and recording the battery voltage with time stamps into a log stored in an on-board memory unit of the handheld tool to track battery consumption as a function of time, wherein the battery consumption as the function of time correlates to a severity of the unintentional muscle tremors and is indicative of an amount of correction imparted by the at least one motor while stabilizing the tremor motions.

* * * * *